US005690928A

United States Patent [19]
Heimbrook et al.

[11] Patent Number: 5,690,928
[45] Date of Patent: Nov. 25, 1997

[54] METHOD OF TREATING BLADDER CANCER CELLS

[75] Inventors: David C. Heimbrook, Ringoes, N.J.; Allen I. Oliff, Gwynedd Valley, Pa.; Steven M. Stirdivant, Warrington, Pa.; Janet Ahern, Horsham, Pa.

[73] Assignee: Merck & Co., Inc., Rahway, N.J.

[21] Appl. No.: 224,422

[22] Filed: Apr. 11, 1994

Related U.S. Application Data

[63] Continuation of Ser. No. 669,269, Mar. 14, 1991, abandoned, which is a continuation-in-part of Ser. No. 542,281, Jun. 21, 1990, abandoned.

[51] Int. Cl.$^6$ .................................................. A61K 38/45
[52] U.S. Cl. ..................... 424/94.5; 435/69.7; 514/12; 530/412; 530/413; 530/418
[58] Field of Search ........................ 424/94.5; 514/12; 435/69.7, 194; 530/402, 420, 399, 412, 413, 418

[56] References Cited

U.S. PATENT DOCUMENTS

| | | | |
|---|---|---|---|
| 4,518,584 | 5/1985 | Mark et al. | 424/85.2 |
| 4,545,985 | 10/1985 | Pastan et al. | 514/2 |
| 4,664,911 | 5/1987 | Uhr et al. | 424/182.1 |
| 4,675,382 | 6/1987 | Murphy et al. | 530/350 |
| 4,742,003 | 5/1988 | Derynck et al. | 435/69.4 |
| 4,892,827 | 1/1990 | Pastan et al. | 435/193 |

FOREIGN PATENT DOCUMENTS

| | | |
|---|---|---|
| 192811 | 9/1986 | European Pat. Off. . |
| 234599 | 2/1987 | European Pat. Off. . |
| 261671 | 3/1988 | European Pat. Off. . |
| 0383599 | 8/1990 | European Pat. Off. . |
| 0389043 | 9/1990 | European Pat. Off. . |
| WO88/00837 | 2/1988 | WIPO . |

OTHER PUBLICATIONS

Allured, V.S. et al., Structure of exototoxin A of *Pseudomonas aeruginosa* at 3.0–Angstrom resolution, (1985), Proc. Natl. Acad. Sci. (Biophysics), 83, pp. 1320–1324.

Berger, M.S. et al., Biological Abstract AB. #85069842 (1987).

Chaudhary, V.K. et al., Pseudomonas exotoxin contains a specific sequence at the carboxyl terminus that is required for cytotoxicity, (1990), Proc. Natl. Acad. Sci. (Biochemistry), 87, pp. 308–312.

Chaudhary, V.K. et al., Role of domain II of Pseudomonas exotoxin in the secretion of proteins into the periplasm and medium by *Escherichia coli*, (1988), Proc. Natl. Acad. Sci. (Biochemistry), 85, pp. 2939–2943.

Chaudhary, V.K. et al., Activity of a recombinant fusion protein between transforming growth factor type a and *Pseudomonas toxin*, (1987), Proc. Natl. Acad. Sci. (Genetics), 84, pp. 4538–4542.

Edwards, G.M. et al., Epidermal Growth Factor Receptor Binding Is Affected by Structural Determinants in the Toxin Domain of Transforming Growth Factor–Alpha–Pseudomonas Exotoxin Fusion Proteins, (1989), Molecular and Cellular Biology, 9, No. 7, pp. 2860–2867.

Gusterson, B. et al., Evidence for Increased Epidermal Growth Factor Receptors in Human Sarcomas, (1985), Int. J. Cancer, 36, pp. 689–693.

Heimbrook, D.C. et al., Transforming Growth factor a–Pseudomonas exotoxin fusion protein prolongs survival of nude mice bearing tumor xenografts, (1990), Proc. Natl. Acad. Sci. (Med. Sciences), 87, pp. 4697–4701.

Hwang, J. et al., Functional Domains of Pseudomonas Exotoxin Identified by Deletion Analysis of the Gene Expressed in *E. coli*, (1987), Cell, 48, pp. 129–136.

Jinno, Y. et al., Domain II Mutants of Pseudomonas Exotoxin Deficient in Translocation, (1989), J. Biol. Chem., 17, pp. 15953–15959.

Madshus, I.H. et al., Effects of Eliminating a Disulfide Bridge within Domain II of *Pseudomonas aeruginosa* Exotoxin A, (1989), Infection and Immunity, 57, No. 7, pp. 1873–1878.

Murphy, J.R. et al., Genetic construction, expression, and melanoma–selective cytotoxicity of a diphtheria toxin–related a–melanocyte–stimulating hormone fusion protein, (1986), Proc. Natl. Acad. Sci. (Genetics), 83, pp. 8258–8262.

Neal, D.E. et al., Epidermal–Growth–Factor Receptors in Human Bladder Cancer: Comparison of Invasive and Superficial Tumours, (Feb. 16, 1985), The Lancet, 1(8425), pp. 366–368.

Pai, L.H. et al., Antitumor Activity of a Transforming Growth Factor a–Pseudomonas Exotoxin Fusion Protein (TGF–a–PE40), (1991), Cancer Research, 51, pp. 2808–2812.

Pastan, I. and FitzGerald, D., Pseudomonas Exotoxin: Chimeric Toxins, (1989), J. Biol. Chem., 264, pp. 15157–15160.

Raghavan, D. et al., Biology and Management of Bladder Cancer, (1990), New England J. Med., 322, No. 16, pp. 1129–1138.

Sherwin, S.A. et al., High–Molecular Weight Transforming Growth Factor Activity in the Urine of Patients with Disseminated Cancer, (1983), Cancer Research, 43, pp. 403–407.

Siegall, C.B. et al., Functional Analysis of Domains II, Ib, and III of Pseudomonas Exotoxin, (1989), J. Biol. Chem., 264, No. 24, pp. 14256–14261.

Spooner, R.A. and Lord, J. M., Immunotoxins: status and prospects, (1990), Tibtech, 8, pp. 189–193.

(List continued on next page.)

*Primary Examiner*—Stephen Walsh
*Assistant Examiner*—Karen E. Brown
*Attorney, Agent, or Firm*—David A. Muthard; Mark R. Daniel

[57] ABSTRACT

Methods and compositions for treating bladder cancer using TGF-alpha or EGF fused to $PE_{40}$ or cysteine modified derivatives are taught. Also, a method of producing TGF-alpha-$PE_{40}$ derivatives of enhanced potency is described.

20 Claims, 1 Drawing Sheet

OTHER PUBLICATIONS

Todaro, G.J. et al., Transforming growth factors produced by certain human tumor cells: Polypeptides that interact with epidermal growth factor receptors, (1980), Proc. Natl. Acad. Sci. (Cell Biol.), 77, No. 9, pp. 5258–5262.

Winter, G. et al., Redesigning enzyme structure by site-directed mutagenesis: tyrosyl tRNA synthetase and ATP binding, (1982), Nature, 299, pp. 756–758.

Schulz et al, pp. 14–16 in *Principles of Protein Structure*, Springer–Verlag (NY) (1979).

METHOD OF TREATING BLADDER CANCER CELLS

RELATED APPLICATION

This is a continuation of application Ser. No. 07/669,269, now abandoned, filed Mar. 14, 1991 which is a continuation-in-part of patent application Ser. No. 07/542,281 filed Jun. 21, 1990, now abandoned.

BACKGROUND OF THE INVENTION

Traditional cancer chemotherapy relies on the ability of drugs to kill minor cells in cancer patients. Unfortunately, these same drugs frequently kill normal cells as well as the tumor cells. The extent to which a cancer drag kills tumor cells rather than normal cells is an indication of the compound's degree of selectivity for tumor cells. One method of increasing the tumor cell selectivity of cancer drugs is to deliver drugs preferentially to the tumor cells while avoiding normal cell populations. Another term for the selective delivery of chemotherapeutic agents to specific cell populations is "targeting". Drug targeting to tumor cells can be accomplished in several ways. One method relies on the presence of specific receptor molecules found on the surface of tumor cells. Other molecules, referred to as "targeting agents", can recognize and bind to these cell surface receptors. These "targeting agents" include, e.g., antibodies, growth factors, or hormones. "Targeting agents" which recognize and bind to specific cell surface receptors are said to target the cells which possess those receptors. For example, bladder tumor cells possess a protein on their surfaces called the epidermal growth factor receptor. Transforming growth factor-alpha (TGF-alpha) recognizes and binds to the EGF receptor on bladder tumor cells. TGF-alpha is therefore, a "targeting agent" for these tumor cells.

"Targeting agents" by themselves do not kill tumor cells. Other molecules including cellular poisons or toxins can be linked to "targeting agents" to create hybrid molecules that possess both tumor cell targeting and cellular toxin domains. These hybrid molecules function as tumor cell selective poisons by virtue of their abilities to target tumor cells and then kill those cells via their toxin component. Some of the most potent cellular poisons used in constructing these hybrid molecules are bacterial toxins that inhibit protein synthesis in mammalian cells. Pseudomonas exotoxin A is one of these bacterial toxins, and has been used to construct hybrid "targeting-toxin" molecules (U.S. Pat. No. 4,545,985).

Pseudomonas exotoxin A intoxicates mammalian cells by first binding to the cell's surface, then entering the cell cytoplasm and inactivating elongation factor 2 which is a cellular protein required for protein synthesis. Pseudomonas exotoxin A has been used to construct anticancer hybrid molecules using monoclonal antibodies and protein hormones. However, one problem with these hybrid molecules is that they exhibit toxicity towards normal cells. At least part of the toxicity associated with hybrid molecules containing pseudomonas exotoxin A is due to the ability of pseudomonas exotoxin A by itself to bind to and enter many types of mammalian cells. Therefore, hybrid molecules formed between pseudomonas exotoxin A and specific "targeting agents" can bind to many normal cells in addition to the cells recognized by the "targeting agent". One method of dealing with this problem is to modify pseudomonas exotoxin A so that it is no longer capable of binding to normal cells. This can be accomplished by removing that portion of the pseudomonas exotoxin A molecule which is responsible for its cellular binding activity. A truncated form of the pseudomonas exotoxin A molecule has been prepared which retains the ability to inactivate elongation factor 2 but no longer is capable of binding to mammalian cells. This modified pseudomonas exotoxin A molecule is called pseudomonas exotoxin-40 or $PE_{40}$ (Hwang, et al., Cell 48:129–136 1987).

$PE_{40}$ has been linked to several targeting molecules including TGF-alpha (Chaudhary, et al., PNAS USA 84:4583–4542 1987). In the case of TGF-alpha, hybrid molecules containing $PE_{40}$ and TGF-alpha domains are capable of specifically binding to tumor cells that possess EGF receptors and intoxicating these cells via inhibiting protein synthesis. In order for this hybrid molecule to efficiently bind to the EGF receptor it must assume the proper conformation. Efficient receptor binding is also dependent on having the "targeting domain" properly exposed so that it is accessible for binding. When TGF-alpha and $PE_{40}$ hybrid molecules are produced as fusion proteins in bacteria using recombinant DNA techniques the majority of hybrid molecules exhibit poor EGF receptor binding activity.

DISCLOSURE STATEMENT

1. U.S. Pat. No. 4,545,985 teaches that pseudomonas exotoxin A can be chemically conjugated to an antibody or to epidermal growth factor. While this patent further teaches that these conjugates can be used to kill human tumor cells, these chemically linked toxins have been shown to have undesirable, nonspecific levels of activity.

2. U.S. Pat. No. 4,664,911 teaches that antibodies can be conjugated to the A chain or the B chain of ricin which is a toxin obtained from plants. U.S. Pat. No. 4,664,911 further teaches that these conjugates can be used to kill human tumor cells.

3. U.S. Pat. No. 4,675,382 teaches that hormones such as melanocyte stimulating hormone (MSH) can be linked to a portion of the diphtheria toxin protein via peptide bonds. U.S. Pat. No. 4,675,382 further teaches that the genes which encode these proteins can be joined together to direct the synthesis of a hybrid fusion protein using recombinant DNA techniques. This fusion protein has the ability to bind to cells that possess MSH receptors.

4. Murphy, et al., PNAS USA 83:8258–8262 1986, Genetic construction, expression, and melanoma-selective cytotoxicity of a diphtheria toxin-related alpha-melanocyte-stimulating hormone fusion protein. This article teaches that a hybrid fusion protein produced in bacteria using recombinant DNA technology and consisting of a portion of the diphtheria toxin protein joined to alpha-melanocyte-stimulating hormone will bind to and kill human melanoma cells.

5. Allured, et al., PNAS USA 83:1320–1324 1986, Structure of exotoxin A of Pseudomonas aeruginosa at 3.0 Angstrom. This article teaches the three dimensional structure of the pseudomonas exotoxin A protein.

6. Hwang, et al., Cell 48:129–136 1987, Functional Domains of Pseudomonas Exotoxin Identified by Deletion Analysis of the Gene Expressed in *E. Coli*. This article teaches that the pseudomonas exotoxin A protein can be divided into three distinct functional domains responsible for: binding to mammalian cells, translocating the toxin protein across lysosomal membranes, and ADP ribosylating elongation factor 2 inside mammalian cells. This article further teaches that these functional domains correspond to distinct regions of the pseudomonas exotoxin A protein.

7. Chaudhary, et al., PNAS USA 84:4538–4542 1987, Activity of a recombinant fusion protein between transforming growth factor type alpha and Pseudomonas toxin. This article teaches that hybrid fusion proteins formed between PE-40 and transforming growth factor-alpha and produced in bacteria using recombinant DNA techniques will bind to and kill human tumor cells possessing epidermal growth factor receptors.

8. European patent application 0 261 671, published 30 Mar. 1988, teaches that a portion of the pseudomonas exotoxin A protein can be produced which lacks the cellular binding function of the whole pseudomonas exotoxin A protein but possesses the translocating and ADP ribosylating functions of the whole pseudomonas exotoxin A protein. The portion of the pseudomonas exotoxin A protein that retains the translocating and ADP ribosylating functions of the whole pseudomonas exotoxin A protein is called pseudomonas exotoxin-40 or PE-40. PE-40 consists of amino acid residues 252–613 of the whole pseudomonas exotoxin A protein as defined in Gray, et al., PNAS USA 81:2645–2649 1984. This patent application further teaches that PE-40 can be linked to transforming growth factor-alpha to form a hybrid fusion protein produced in bacteria using recombinant DNA techniques.

9. Kelley, et al., PNAS USA 85:3980–3984 1988, Interleukin 2-diphtheria toxin fusion protein can abolish cell-mediated immunity in vivo. This article teaches that a hybrid fusion protein produced in bacteria using recombinant DNA technology and consisting of a portion of the diphtheria toxin protein joined to interleukin 2 functions in mice to suppress cell mediated immunity.

10. Bailon, Biotechnology, pp. 1326–1329 November 1988. Purification and Partial Characterization of an Interleukin 2-Pseudomonas Exotoxin Fusion Protein. This article teaches that hybrid fusion proteins formed between PE-40 and interleukin 2 and produced in bacteria using recombinant DNA techniques will bind to and kill human cell lines possessing interleukin 2 receptors.

11. Edwards, et al., Mol. Cell. Biol. 9:2860–2867 1989 describe the preparation of the modified TGF-alpha-$PE_{40}$ hybrid molecules that have been found to have utility in treating bladder tumor cells.

12. Heimbrook, et al., Proc. Natl. Acad. Sci. USA 87: 4697–4701 1990 describe the in vivo efficacy of modified TGF-alpha-$PE_{40}$ in significantly prolonging the survival of mice containing human tumor cell xenografts.

OBJECTS OF THE INVENTION

It is an object of the present invention to provide modifications of $PE_{40}$ which permit efficient binding of hybrid molecules formed between TGF-alpha and modified $PE_{40}$ molecules to cellular receptors on bladder tumor cells that recognize the TGF-alpha "targeting agent". It is another object of this invention to provide a method for selectively killing bladder tumor cells. A further object is to provide a hybrid molecule of enhanced potency formed between TGF-alpha and modified $PE_{40}$ molecules. Another object of the present invention is to provide pharmaceutical compositions containing as active ingredient a hybrid molecule containing a $PE_{40}$ domain (or region) wherein the $PE_{40}$ domain has been modified to improve binding of the hybrid protein to the epidermal growth factor receptor on bladder tumor cells. These and other objects of the present invention will be apparent from the following description.

SUMMARY OF INVENTION

The present invention provides a hybrid molecule comprising a modified $PE_{40}$ domain bonded to a TGF-alpha targeting domain. The modified $PE_{40}$ domain improves the receptor binding activity of this hybrid molecule. Substitution of other neutral amino acids such as, e.g., alanine, for the cysteine residues in $PE_{40}$, or deletion of cysteine residues, improves binding of the hybrid molecule to the receptors recognized by the targeting domain. The hybrid molecules of the present invention bind more efficiently to targeted receptors on human tumor cells than hybrid molecules having unmodified $PE_{40}$, and have utility in killing bladder tumor cells.

DETAILED DESCRIPTION OF THE INVENTION

Figure 1:
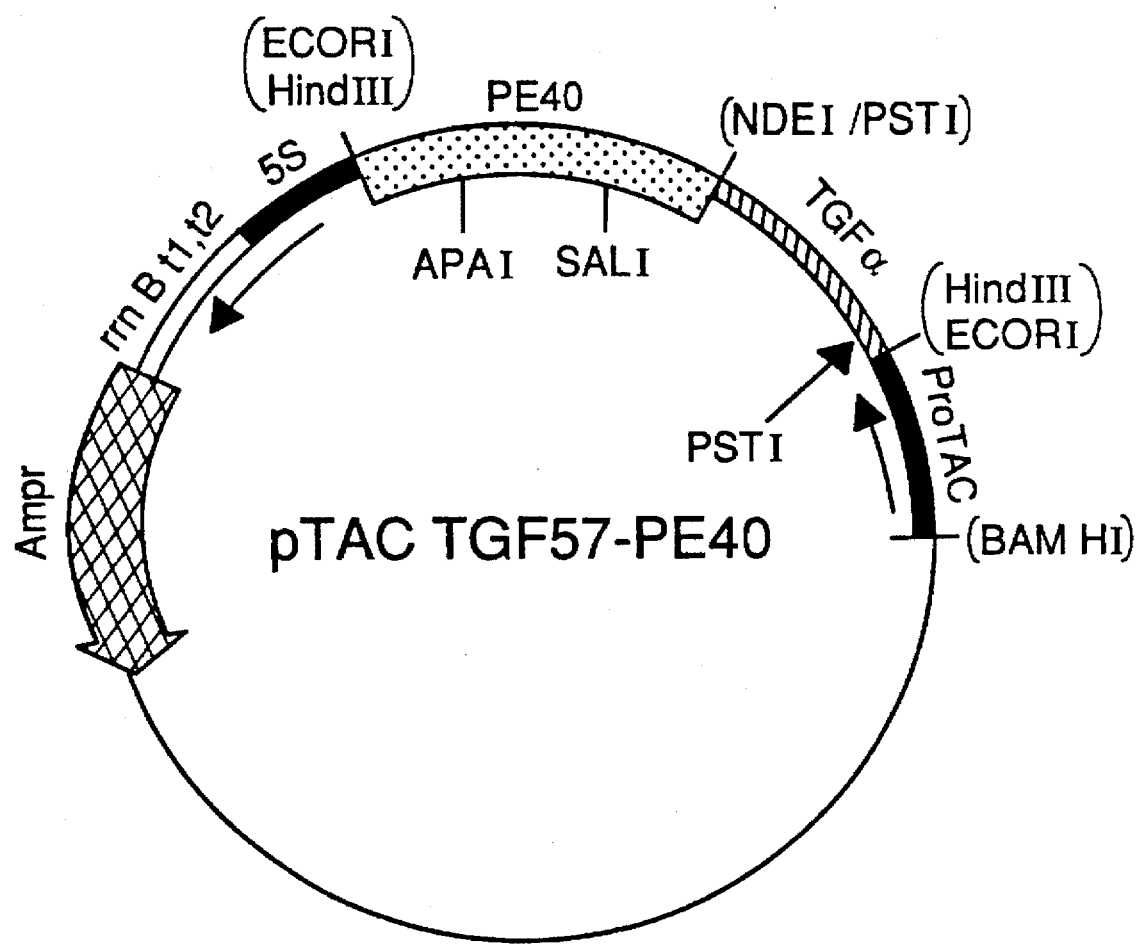
FIG. 1: Plasmid Map of the PTAC TGF57-PE40 Construction: A diagramatic representation of the plasmid utilized as the precursor to the modified recombinant TGF-alpha-$PE_{40}$ containing clones.

Hybrid molecules formed between TGF-alpha and $PE_{40}$ are characterized in three primary assay systems. These assays include: 1—ADP ribosylation of elongation factor 2 which measures the enzymatic activity of TGF-alpha-$PE_{40}$ that inhibits mammalian cell protein synthesis, 2—inhibition of radiolabeled EGF binding to the EGF receptor on membrane vesicles from A431 cells which measures the EGF receptor binding activity of TGF-alpha-$PE_{40}$, and 3—cell proliferation as assessed by conversion of 3-[4,5-dimethylthiazol-2-yl]-2,5-diphenyltetrazolium bromide (MTT) to formazan which is used to measure the survival of tumor cells following exposure to TGF-alpha-$PE_{40}$. These assays are performed as previously described (Dominic, et al., Infection and Immunity 16:832–841 1977, Cohen, et al., J. Biol. Chem. 257:1523–1531 1982, Riemen, et al., Peptides 8:877–885 1987, Mosmann J. Immunol. Methods 65:55–63 1983).

To create new TGF-alpha-$PE_{40}$ hybrid molecules with superior receptor binding characteristics we first produced a series of recombinant DNA molecules that encoded either TGF-alpha-$PE_{40}$ or specifically modified versions of TGF-alpha-$PE_{40}$. The original or parental TGF-alpha-$PE_{40}$ gene was molecularly cloned in a bacterial TAC expression plasmid vector (pTAC TGF57-PE40) using distinct segments of cloned DNA as described in Example 1. The pTAC TGF57-PE40 DNA clone was used as the starting reagent for constructing specifically modified versions of TGF-alpha-$PE_{40}$ DNA. The specific modifications of the pTAC TGF57-PE40 DNA involve site specific mutations in the DNA coding sequence required to replace two or four of the cysteine codons within the $PE_{40}$ domain of the pTAC TGF57-PE40 DNA with codons for other amino acids. Alternatively, the site specific mutations can be engineered to delete two or four of the cysteine codons within the $PE_{40}$ domain of pTAC TGF57-PE40. The site specific mutations in the pTAC TGF57-PE40 DNA were constructed using the methods of Winter, et al., Nature 299:756–758 1982. Specific examples of the mutated pTAC TGF57-PE40 DNAs are presented in Example 3. The amino acid sequence of the hybrid protein encoded by the pTAC TFG57-PE40 DNA is presented in Table 2. The four cysteine residues in the $PE_{40}$ domain of the parental TGF-alpha-$PE_{40}$ hybrid protein are designated residues $Cys^{265}$, $Cys^{287}$, $Cys^{372}$, and $Cys^{379}$ (Table 2). Amino acid residues in the $PE_{40}$ domain are numbered as defined in Gray, et al, PNAS USA 81:2645–2649 (1984). The modified TGF-alpha-$PE_{40}$ hybrid proteins generated from the specifically mutated pTAC TGF57-PE40 DNA contain substitutions or deletions of the two N-terminal $PE_{40}$ residues [$Cys^{265}$ and $Cys^{287}$] or the two C-terminal residues [$Cys^{372}$ and $Cys^{379}$], or both [$Cys^{265}$, $Cys^{287}$, $Cys^{372}$, and $Cys^{379}$]. To simplify the nomenclature for describing the modified hybrid proteins produced from these mutated pTAC TGF57-PE40 DNAs we have designated the amino acid residues at the N-terminal positions the "A" locus and the residues at the C-terminal positions the "B" locus. When cysteine residues are present at the two N-terminal $PE_{40}$ positions as in parental TGF-alpha-$PE_{40}$ hybrid molecule, the locus is capitalized (i.e. "A"). When these cysteines are substituted with other neutral amino acids such as, for example, glycine, alanine, phenylalanine, valine, leucine, isoleucine, tyrosine, histidine, tryptophan, serine, threonine or methionine, or deleted from the N-terminal positions, the locus is represented by a lower case "a". Similarly, if the amino acid residues at the two C-terminal positions are cysteines the locus is represented by an upper case "B" while a lower case "b" represents this locus when the amino acid residues at these positions are substituted with other amino acids or deleted. Thus when all four cysteine residues in the $PE_{40}$ domain of TGF-alpha-$PE_{40}$ are substituted with alanines the modified hybrid protein is designated TGF-alpha-$PE_{40}$ ab. In a similar fashion the parental TGF-alpha-$PE_{40}$ hybrid protein with cysteines at amino acid residue positions 265, 287, 372 and 379 can be designated TGF-alpha-$PE_{40}$ AB.

Both the TGF-alpha-$PE_{40}$ AB hybrid protein and the modified TGF-alpha-$PE_{40}$ hybrid proteins are produced in E. coli using the TAC expression vector system described by Linemeyer, et al., Bio-Technology 5:960–965 1987. The recombinant hybrid proteins produced in these bacteria are harvested and purified by lysing the bacteria in guanidine hydrochloride followed by the addition of sodium sulphite and sodium tetrathionate. This reaction mixture is subsequently dialyzed and urea is added to solubilize proteins that have precipitated out of solution. The mixture is next centrifuged to remove insoluble proteins and the recombinant hybrid TGF-alpha-$PE_{40}$ proteins are separated using ion exchange chromatography followed by size exclusion chromatography, followed once again by ion exchange chromatography. The purified TGF-alpha-$PE_{40}$ hybrid proteins are next exposed to reducing agents such as beta-mercaptoethanol in order to permit disulfide bonds to form within the hybrid protein between pairs of cysteine residues. Finally, the refolded hybrid proteins are subjected to size exclusion and ion exchange chromatography to isolate highly pure TGF-alpha-$PE_{40}$ protein. The precise details of this purification scheme are described in Example 4. Once purified and refolded the biologic activity of these hybrid proteins can be characterized using the ADP ribosylation, EGF receptor binding, and cell proliferation assays described above.

Alternatively, and preferably, the hybrid proteins TGF-alpha-$PE_{40}$ AB, TGF-alpha-$PE_{40}$ Ab, TGF-alpha-$PE_{40}$ aB and TGF-alpha-$PE_{40}$ ab are produced in transformed bacteria. The bacteria are harvested and the cell paste is lysed and treated, preferably by centrifugation, to remove debris and undesired proteins. The desired hybrid protein then is precipitated by addition of a sulfate salt, preferably $(NH_4)_2SO_4$, to the supernatant liquid. The precipitate is sulfitolyzed, refolded by addition of excess β-mercaptoethanol, concentrated and separated by ion-exchange chromatography and metal-chelating chromatography. Specific details are disclosed in Example 5.

An important utility of TGF-alpha modified $PE_{40}$ lies in its ability to bind to and kill human bladder tumor cells. The anti-cancer proteins described herein have utility in killing bladder cancer cells and are used for this purpose in the form of a solution or suspension in a physiologically acceptable liquid such as, for example, sterile water, water for injection, saline or, preferably, buffered saline or buffered saline containing a carrier protein such as, for example, human serum albumin, e.g., phosphate buffered saline or PBS containing human serum albumin. The solution or suspension contains from about 0.1 mg to about 10 mg of anti-cancer hybrid protein per 60 ml of physiologically acceptable liquid. More preferably, it contains from about 0.5 mg to about 5 mg per 60 ml, and most preferably, it contains from about 2 mg to about 4 mg per 60 ml of physiologically acceptable liquid.

The method of the present invention consists in contacting the bladder cancer cells with the solution or suspension containing the anti-cancer proteins described herein for a period of from less than an hour, for example, about 30 minutes, to a period of several hours, for example, up to about four hours, at ambient temperature. In the case of laboratory animals the solution or suspension is administered via a trans-urethral catheter.

While the use of TGF-alpha modified $PE_{40}$ hybrid molecules is described herein and in the following examples, it is to be understood that the scope of the present invention includes as targeting agents TGF-alpha, EGF, other members of the EGF family of peptide hormones that bind to the EGF receptor on bladder tumor cells, Shope fibroma virus growth factor, and vaccinia virus growth factor and that the toxin to which the targeting agent is coupled also includes $PE_{40}$, diphtheria toxin, ricin toxin or other members of the ADP-ribosylating class of mammalian cell poisons.

The following examples illustrate the present invention without, however, limiting the same thereto. All of the enzymatic reactions required for molecular biology manipulations, unless otherwise specified, were carded out as described in Maniatis, et al. (1982) In: Molecular Cloning: A Laboratory Manual, Cold Spring Harbor Press.

EXAMPLE 1

Construction of recombinant DNA clones containing TGF-alpha-$PE_{40}$ DNA

The TGF-alpha DNA segment was constructed using three sets of synthetic oligonucleotides as described by Defeo-Jones, et al., Molecular and Cellular Biology 8:2999–3007 1988. This synthetic TGF-alpha gene was cloned into pUC-19. DNA from the pUC-19 clone containing recombinant human TGF-alpha was digested with Sph I and Eco RI. The digestion generated a 2.8 kb DNA fragment containing all of pUC-19 and the 5' portion of TGF-alpha. The 2.8 kb fragment was purified and isolated by gel electrophoresis. An Eco RI to Sph I oligonucleotide cassette was synthesized. This synthetic cassette had the sequence indicated below:

5'-CGGACCTCCTGGCTGCGCATCTAGG-3'

3'-GTACGCCTGGAGGACCGACGCGTAGATCCTTAA-5'

For convenience, this oligonucleotide cassette was named 57. Cassette 57 was annealed and ligated to the TGF-alpha containing 2.8 kb fragment forming a circularized plasmid. Clones which contained the cassette were identified by hybridization to radiolabeled cassette 57 DNA. The presence of human TGF-alpha was confirmed by DNA sequencing. Sequencing also confirmed the presence of a newly introduced Fsp I site at the 3' end of the TGF-alpha sequence. This plasmid, named TGF-alpha-57/pUC-19, was digested with HinD III and Fsp I which generated a 168 bp fragment containing the TGF-alpha gene (TGF-alpha-57). A separate preparation of pUC-19 was digested with HinD III and Eco RI which generated a 2.68 kb pUC-19 vector DNA. The $PE_{40}$ DNA was isolated from plasmid pVC 8 (Chaudhary, et al., PNAS USA 84:4538–4542 1987). pVC 8 was digested using Nde I. A flush end was then generated on this DNA by using the standard conditions of the Klenow reaction (Maniatis, et al., supra, p.113). The flush-ended DNA was then subjected to a second digestion with Eco RI to generate a 1.3 kb Eco RI to Nde I (flush ended) fragment containing $PE_{40}$. The TGF-alpha-57 HinD III to Fsp I fragment (168 bp) was ligated to the 2.68 kb pUC-19 vector. Following overnight incubabion, the 1.3 kb EcoRI to Nde I (flush ended) $PE_{40}$ DNA fragment was added to the ligation mixture. This second ligation was allowed to proceed overnight. The ligation reaction product was then used to transform JM 109 cells. Clones containing TGF-alpha-57 $PE_{40}$ in pUC-19 were identified by hybridization to radiolabeled TGF-alpha-57 $PE_{40}$ DNA and the DNA from this clone was isolated. The TGF-alpha-57 $PE_{40}$ was removed from the pUC-19 vector and transferred to a TAC vector system described by Linemeyer, et al., Bio-Technology 5:960–965 (1987). The TGF-alpha-57 $PE_{40}$ in pUC-19 was digested with HinD III and Eco RI to generate a 1.5 kb fragment containing TGF-alpha-57 $PE_{40}$. A flush end was generated on this DNA fragment using standard Klenow reaction conditions (Maniatis, et al., loc. cit.). The TAC vector was digested with Hind III and Eco RI. A flush end was generated on the digested TAG vector DNA using standard Klenow reaction conditions (Maniatis, et al., loc. cit.). The 2.7 kb flush ended vector was isolated using gel electrophoresis. The flush ended TGF-alpha-57 $PE_{40}$ fragment was then ligated to the flush ended TAC vector. The plasmid generated by this ligation was used to transform JM 109 cells. Candidate clones containing TGF-alpha-57 $PE_{40}$ were identified by hybridization as indicated above and sequenced. The clone containing the desired construction was named pTAC TGF57-PE40. The plasmid generated by these manipulations is depicted in FIG. 1. The nucleotide sequence of the amino acid codons of the TGF-alpha-$PE_{40}$ fusion protein encoded in the pTAC TGF-57-PE40 DNA are depicted in Table 1. The amino acid sequence encoded by the TGF-57-PE40 gene is shown in Table 2.

EXAMPLE 2

Construction of modified versions of recombinant TGF-alpha-$PE_{40}$ containing DNA clones: Substitution of alanines for cysteines TGF-alpha-$PE_{40}$ aB The clone pTAC TGF57-PE40 was digested with SphI and BamHI and the 748 bp SphI-BamHI fragment (specifying the C-terminal 4 amino acids of TGF-alpha, 4 linker amino acids and the N-terminal 240 amino acids of $PE_{40}$) was isolated. M13 mp19 vector DNA was cut with SphI and BamHI and the vector DNA was isolated. The 748 bp SphI-BamHI TGF-alpha-$PE_{40}$ fragment was ligated into the M13 vector DNA overnight at 15° C. Bacterial host cells were transformed with this ligation mixture, candidate clones were isolated and their plasmid DNA was sequenced to insure that these clones contained the proper recombinant DNAs. Single stranded DNA was prepared for mutagenesis.

An oligonucleotide (oligo #132) was synthesized and used in site directed mutagenesis to introduce a HpaI site into the TGF-alpha-$PE_{40}$ DNA at amino acid position 272 of $PE_{40}$:

5' CTGGAGACGTTAACCCGTC 3' (oligo #132)

One consequence of this site directed mutagenesis was the conversion of residue number 272 in $PE_{40}$ from phenylalanine to leucine. The mutagenesis was performed as described by Winter, et al., Nature, 299:756–758 1982.

A candidate clone containing the newly created HpaI site was isolated and sequenced to validate the presence of the mutated genetic sequence. This clone was then cut with SphI and SalI. A 198 bp fragment specifying the C-terminal 5 amino acids of TGF-alpha and the N-terminal 61 amino acids of $PE_{40}$ and containing the newly introduced HpaI site was isolated and subcloned back into the parent pTAC TGF57-PE40 plasmid at the SphI-SalI sites. Bacterial host cells were transformed, a candidate clone was isolated and its plasmid DNA was sequenced to insure that this clone contained the proper recombinant DNA. For convenience this clone was named pTAC TGF57-PE40-132. pTAC TGF57-PE40-132 was digested with SphI and HpaI and a 3.96 Kb DNA fragment was isolated. A synthetic oligonucleotide cassette (oligo #153) spanning the C-terminal 5 amino acids of TGF-alpha and the N-terminal 32 amino acids of $PE_{40}$ and containing SphI and HpaI compatible ends was synthesized and ligated to the digested pTAC TGF57-PE40-132:

5' CGGACCTCCTGGCCATGGCCGAAGAGGGCGGCAGC
3' GTACGCCTGGAGGACCGGTACCGGCTTCTCCCGCCGTCG
CTGGCCGCGCTGACCGCGCACCAGGCTGCACACCTGCCGC
GACCGGCGCGACTGGCGCGTGGTCCGACGTGTGGACGGCG
TGGAGACGTT 3'
ACCTCTGCAA 5' (oligo #153)

This oligonucleotide cassette incorporated a change in the TGF-alpha-$PE_{40}$ DNA so that the codon specifying alanine at residue 51 was eliminated and the codon specifying cysteine at residue 264 of $PE_{40}$ now specified alanine. For convenience this plasmid DNA was called pTAC TGF57-PE40-132,153. Bacterial host cells were transformed with pTAC TGF57-PE40-132, 153 DNA. Candidate clones were identified by hybridization, isolated and their plasmid DNA was sequenced to insure that it contained the proper recombinant DNA.

pTAC TGF57-PE40-132,153 DNA was digested with HpaI and SalI and a 3.95 Kb vector DNA was isolated. A synthetic oligonucleotide cassette (oligo #142) spanning amino acid residues 272 to 309 of $PE_{40}$ and containing HpaI and SalI compatible ends was synthesized and ligated to the 3.95 Kb pTAC TGF/PE40 132,153 DNA.

5' AACCCGTCATCGCCAGCCGCGCGGCTGGGAACAACTGGAG
3' TTGGGCAGTAGCGGTCGGCGCGCCGACCCTTGTTGACCTC
CAGGCTGGCTATCCGGTGCAGCGGCTGGTCGCCCTCTACC
GTCCGACCGATAGGCCACGTCGCCGACCAGCGGGAGATGG
TGGCGGCGCGGCTGTCGTGGAACCAGG 3'
ACCGCCGCGCCGACAGCACCTTGGTCCAGCT 5' (oligo #142)

This oligonucleotide cassette changed the codon specifying cysteine at residue 287 so that this codon now specified alanine. For convenience this mutated plasmid DNA was called pTAC TGF57-PE40-132,153,142. Bacterial host cells were transformed with this plasmid and candidate clones were identified by hybridization. These clones were isolated and their plasmid DNA was sequenced to insure that it contained the proper recombinant DNA. The pTAC TGF57-

PE40-132,153,142 plasmid encodes the TGF-alpha-PE$_{40}$ variant with both N-terminal cysteines at locus "A" replaced by alanines. Therefore, following the nomenclature described previously this modified version of TGF-alpha-PE$_{40}$ is called TGF-alpha-PE$_{40}$ aB. The amino acid sequence encoded by the TGF-alpha-PE$_{40}$ aB gene is shown in Table 3.

TGF-alpha-PE$_{40}$ Ab

The clone pTAC TGF57-PE40 was digested with SphI and BamHI and the 748 bp SphI-BamHI fragment (specifying the C-terminal 4 amino acids of TGF-alpha 4 linker amino acids and the N-terminal 240 amino acids of PE$_{40}$) was isolated. M13 mp19 vector DNA was cut with SphI and BamHI and the vector DNA was isolated. The 748 bp SphI-BamHI TGF-alpha-PE$_{40}$ fragment was ligated into the M13 vector DNA overnight at 15° C. Bacterial host cells were transformed with this ligation mixture, candidate clones were isolated and their plasmid DNA was sequenced to insure that these clones contained the proper recombinant DNAs. Single stranded DNA was prepared for mutagenesis.

An oligonucleotide (oligo #133) was synthesized and used in site directed mutagenesis to introduce a BsteII site into the TGF-alpha-PE$_{40}$ DNA at amino acid position 369 of PE$_{40}$:

5' GACGTGGTGACCCTGAC 3' (oligo #133)

One consequence of this mutagenesis was the conversion of the serine residue at position 369 of PE$_{40}$ to a threonine.

A DNA clone containing the newly created BsteII site was identified, isolated and sequenced to ensure the presence of the proper recombinant DNA. This clone was next digested with ApaI and SalI restriction enzymes. A 120 bp insert DNA fragment containing the newly created BsteII site was isolated and ligated into pTAC TGF57-PE40 that had also been digested with ApaI and SalI. Bacterial host cells were transformed, and a candidate clone was isolated and sequenced to insure that the proper recombinant DNA was present. This newly created plasmid DNA was called pTAC TGF57-PE40-133. It was digested with BsteII and ApaI and 2.65 Kb vector DNA fragment was isolated.

A BsteII to ApaI oligonucleotide cassette (oligo #155) was synthesized which spanned the region of TGF-alpha-PE$_{40}$ deleted from the pTAC TGF57-PE40-133 clone digested with BsteII and ApaI restriction enzymes. This cassette also specified the nucleotide sequence for BsteII and ApaI compatible ends.

5' GTGACCCTGACCGCGCCGGTCGCCGCCG-
GTGAAGCTGCGGGCC 3'

3' GGACTGGCGCGGCCAGCGGCGGCCACTTCGACGC 5'

(oligo #155)

This oligonucleotide cassette changed the codons for cysteines at residues 372 and 379 of PE$_{40}$ to codons specifying alanines. Oligonucleotide cassette #155 was ligated to the 2.65 Kb vector DNA fragment. Bacterial host cells were transformed and candidate clones were isolated and sequenced to insure that the proper recombinant DNA was present. This newly created DNA clone was called pTAC TGF57-PE40-133,155. It encodes the TGF-alpha-PE$_{40}$ variant with both cysteines at locus "B": replaced by alanines. Therefore, following the nomenclature described previously this modified version of TGF-alpha-PE$_{40}$ is called TGF-alpha-PE$_{40}$ Ab. The amino acid sequence encoded by the TGF-alpha-PE$_{40}$ Ab gene is shown in Table 4.

TGF-alpha-PE$_{40}$ ab

The pTAC-TGF57-PE$_{40}$-132,153,142 plasmid encoding TGF-alpha-PE$_{40}$ aB was digested with SalI and ApaI and the resultant 3.8 Kb vector DNA fragment was isolated. The pTAC TGF57-PE40-133,155 plasmid encoding TGF-alpha-PE$_{40}$ Ab was also digested with SalI and ApaI and the resultant 140 bp DNA fragment containing the cysteine to alanine changes at amino acid residues 372 and 379 of PE$_{40}$ was isolated. These two DNAs were ligated together and used to transform bacterial host cells. Candidate clones were identified by hybridization with a radiolabeled 140 bp DNA from pTAC TGF57-PE$_{40}$-133,155. Plasmid DNA from the candidate clones was isolated and sequenced to insure the presence of the proper recombinant DNA. This newly created DNA clone was called pTAC TGF57-PE40-132,153, 142,133,155. This plasmid encodes the TGF-alpha-PE$_{40}$ variant with all four cysteines at loci "A" and "B" replaced by alanines. Therefore, following the nomenclature described previously this modified version of TGF-alpha-PE$_{40}$ is called TGF-alpha-PE$_{40}$ ab. The amino acid sequence encoded by the TGF-alpha-PE$_{40}$ ab gene is shown in Table 5.

EXAMPLE 3

Construction of modified versions of recombinant TGF-alpha-PE$_{40}$ containing DNA clones: Deletion of cysteine residues TGF-alpha-PE$_{40}$ aB, TGF-alpha-PE$_{40}$ Ab, and TGF-alpha-PE$_{40}$ ab can also be constructed by removing the cysteine residues at locus "A" and/or locus "B". Construction of these versions of TGF-alpha-PE$_{40}$ are accomplished identically as described in Example 2 except that: for TGF-alpha-PE$_{40}$ aB oligonucleotide cassette 153 is changed such that the alanine codon intended for position 265 is deleted and oligonucleotide cassette 142 is changed such that the alanine codon intended for position 287 is deleted. For TGF-alpha-PE$_{40}$ Ab oligonucleotide cassette 155 is changed such that the alanine codons intended for residues 372 and 379 are deleted. For TGF-alpha-PE$_{40}$ ab the DNA fragments used to construct this recombinant gene are taken from the TGF-alpha-PE$_{40}$ aB and TGF-alpha-PE$_{40}$ Ab gene described in this example.

EXAMPLE 4

Production and isolation of recombinant TGF-alpha-PE$_{40}$ fusion proteins

Production of fusion protein

Transformed *E. coli* JM-109 cells were cultured in 1 L shake flasks in 500 ml LB-Broth in the presence of 100 mg/ml ampicillin at 37° C. After the A600 spectrophotometric absorbance value reached 0.6, isopropyl B-D-thiogalactopyranoside was added to a final concentration of 1 mM. After 2 hours the cells were harvested by centrifugation.

S-Sulphonation of fusion protein

The cells were lysed in 8M guanidine hydrochloride, 50 mM Tris pH 8.0, 1 mM EDTA by stirring at room temperature for 2 hours. The lysis mixture was brought to 0.4M sodium sulphite and 0.1M sodium tetrathionate by adding solid reagents and the pH was adjusted to 9.0 with 1M NaOH. The reaction was allowed to proceed at room temperature for 16 hours.

Preparation for chromatography

The protein solution was dialysed against a 10,000 fold excess volume of 1 mM EDTA at 4° C. The mixture was then brought to 6M urea, 50 mM Tris pH 8.0, 50 mM NaCl at room temperature and stirred for 2 hours. Any undissolved material was removed by centrifugation at 32,000×g for 30 minutes.

DEAE F.F. Sepharose Chromatography

The cleared supernatant from the previous step was applied to a 26×40 cm DEAE Fast Flow column (Pharmacia LKB Biotechnology Inc.) equilibrated with 6M urea, 50 mM Tris pH 8.0, 50 mM NaCl at a flow rate of 1 ml/minute. The column was washed with the equilibration buffer until all unabsorbed materials were removed as evidenced by a UV 280 spectrophotometric absorbance below 0.1 in the equilibration buffer as it exits the column. The adsorbed fusion protein was eluted from the column with a 1000 ml 50–350 mM NaCl gradient and then concentrated in a stirred cell Amicon concentrator fitted with a YM-30 membrane.

Sephacryl S-300

The concentrated fusion protein (8 mls) was applied to a 2.6×100 cm Sephacryl S-300 column (Pharmacia LKB Biotechnology Inc.) equilibrated with 6M urea, 50 mM Tris pH 8.0, 50 mM NaCl at a flow rate of 0.25 ml/minute. The column was eluted with additional equilibration buffer and 3 ml fractions collected. Fractions containing TGF-alpha-$PE_{40}$ activity were pooled.

Q-sepharose Chromatography

The pooled fractions from the S-300 column were applied to a 1.6×40 cm Q-sepharose column (Pharmacia LKB Biotechnology, Inc.) equilibrated with 6M urea, 50 mM Tris pH 8.0, 50 mM NaCl at a flow rate of 0.7 ml/minute. The column was washed with the equilibration buffer and then eluted with a 600 ml 50–450 mM NaCl gradient. The fractions containing the TGF-alpha-$PE_{40}$ activity were pooled and then dialysed against 50 mM glycine pH 9.0 and stored at −20° C.

Refolding

A sample of the protein was thawed and diluted to a spectrophotometric absorbance at UV A280=0.1 in 50 mM glycine pH 10.5. Beta-mercaptoethanol was added to give a 4:1 molar ratio over the theoretical number of S-sulphonate groups present in the protein sample. The reaction was allowed to proceed for 16 hours at 4° C. after which time the solution was dialysed against a 10,000 fold excess of physiologically buffered saline and stored at −20° C.

EXAMPLE 5

Production and Isolation of Recombinant TGF-alpha-$PE_{40}$ Fusion Proteins

E. coli strain JM-109, containing the appropriate TGF-alpha-$PE_{40}$ plasmid, was cultured at 37° C. in complex medium (Bauer, et al., Biotechnology and Bioengineering 16 933–41 (1974)) with antibiotic at 100 mg/ml. TGF-$PE_{40}$ expression was induced upon addition of 1 mM isopropylthiogalactoside after the culture had attained an absorbance at 600 nm of 2.5. The culture was harvested by crossflow filtration following a nine hour induction period, and frozen at −70° C.

The cell paste was thawed on ice in 4 volumes of 50 mM sodium phosphate, pH 7.8, to form a suspension that was passed through 4 layers of cheesecloth and then twice through a Matin-Gaulin press at 9,000 psi. The filtered suspension was centrifuged in a Sorvall GS-3 rotor at 9000 rpm (13,000×g) for 30 minutes to remove debris. Saturated ammonium sulfate solution was added to the supernatant liquid dropwise with stirring to a 20% saturation (250 ml/l) at room temperature. The suspension was stirred at 4° C. for 0.5–1 hour and then centrifuged in the CS-3 rotor at 9000 rpm (13,000×g) for 20 minutes.

Saturated ammonium sulfate was added to the supernatant liquid with stirring to a 35% concentration (230 ml/l supernatant). The ammonium sulfate containing solution was stirred at 4° C. for 0.5–1 hour and then centrifuged as above. The pellet was resuspended in 50 mM sodium phosphate, 50% $NH_4SO_4$, pH 7.5 at ¼ of the starting volume, stirred as above and centrifuged in the Sorvall SA-600 at 5,000 rpm (3,600×g) for 15 minutes in polypropylene tubes. The supernatant liquid was discarded and the pellets resuspended at 10 mg protein/ml in 50 mM Tris, 6M guanidine-HCl, pH 9.0 at room temperature.

$Na_2SO_3$ was added to a concentration of 0.4M and $Na_2S_4O_6$ was added to a concentration of 0.1M. The pH was checked; if not 9.0, an appropriate adjustment is made with HCl or NaOH. After stirring overnight at room temperature, the sulfitot 50 mM Gly-Cl, pH 9.0 at 4° C.

The protein was then diluted to 0.1 mg/ml in 50 mM Gly-Cl, pH 10.5 and a 40-fold molar excess of β-mercaptoethanol (87 mM β-Me at 0.1 mg/ml) was added. The mixture was stirred at 4° C. for about 15 hours, and the refolded protein was dialyzed for about 15 hours at 4° C. against 20 mM Tris-Cl, 50 mM NaCl, pH 8.0. The protein was then loaded onto a Q-Sepharose column pre-equilibrated in 20 mM Tris-Cl, 50 mM NaCl, pH 8.0, at 4° C., using about 0.3 ml resin/mg protein, and eluted with a linear salt gradient from 50 mM to 500 mM NaCl in 20 mM Tris-Cl, pH 8.0 (gradient size=6–10 column volumes).

The column fractions were analyzed and pooled by $A_{280}$ UV absorption, gel electrophoresis and Western blots. A metal-chelating column was prepared by treating chelating Sepharose 4B with $CuSO_4$ using 0.3 to 1 ml resin/mg protein. The column was equilibrated with 50 mM Tris-acetate, 1M NaCl, pH 7.0. To assure that no $Cu^{+2}$ was eluting, a second metal-free column of chelating Sepahrose 4B was installed downstream of the $Cu^{2+}$-charged column.

The Q-Sepharose sample pool was diluted 1:2 in 50 mM Tris-acetate, 1M NaCl, pH 7.0, and loaded onto the metal-chelating column at room temperature. The column was washed with one column volume of equilibration buffer, and the protein eluted with a linear gradient of 0 to 70 mM imidazole, maintained at pH 7.0, in the equilibration buffer (gradient size 10 to 40 column volumes).

The column fractions were analyzed and pooled by $A_{280}$ UV absorption, gel electrophoresis and Western blots.

EXAMPLE 6

Eight human bladder carcinoma cell lines were obtained from the American Type Culture Collection (ATCC) as frozen ampoules. They were immediately cultured and passaged as monolayers according to the instructions provided by ATCC. After characterizing the growth rate of each cell line, cells were plated in 96-well plates at the appropriate dilution to form sub-confluent layers in control wells at the end of the assay. The next day these sub-confluent cultures, maintained either on serum-free MEM-a, RPMI 1640 or McCoy's 5A medium, were utilized in a standard cell kill assay (Mosmann, J. Immunol. Methods 65:55–63, 1983; Edwards et al., Mol. Cell. Biol. 9: 2860–2867, 1989). Each cell line was seeded into 96-well plates at 10,000 viable cells per well. Twenty-four hours later, the cells were washed once and placed in serum-free medium containing the test compound under study. Forty-eight hours later the number of surviving cells was quantitated by using an MTT [3-(3, 4-dimethylthiazol-2-yl)-2,5-diphenyltetrazalium bromide] assay as described by Mosmann, supra. The activity of the toxin against each cell line was assessed, and the data are summarized in the following table, with activity against A431 (vulva carcinoma) cells presented for comparison.

Activity Of TGF-Alpha-Pe40 AB (Ex. 5) Against Human Bladder Carcinoma Cell Lines

| Cell Line | $EC_{50}(pM)$* |
|---|---|
| J-82 | 130 |
| RT-4 | 180 |
| 5637 | 180 |
| SCaBER | 230 |
| UMUC-3 | 830 |
| T-24 | 840 |
| TCCSUP | 7,000 |
| HT1197 | 11,500 |
| A431 | 79 |

*concentration (picomoles/liter) that reduces number of cells surviving after 48 hours to 50% of number of control cells.

EXAMPLE 7

Comparison of Several Cancer Cell Lines Against TGF-alpha-$PE_{40}$ AB, TGF-alpha-$PE_{40}$ ab of EX. 4 and TGF-alpha-$PE_{40}$ ab of EX. 5

| | $EC_{50}$'s [pM] | | |
|---|---|---|---|
| | AB | (EX. 4) | (EX. 5) |
| SQUAMOUS CELL | | | |
| A-431 | 39 | 378 | 163 |
| A-431 | 146 | 355 | 161 |
| A-431 | 94 | 314 | 183 |
| A-431 | 77 | 297 | 207 |
| HeLa | 8356 | 310088 | 3988 |
| SCC-4 | 227 | 861 | 445 |
| SCC-9 | 443 | 647 | 218 |
| SCC-15 | 106 | 392 | 193 |
| SCC-25 | 39 | 147 | 67 |
| GLIOBLASTOMA | | | |
| U138MG | 20889 | >316nM | 216609 |
| U373MG | >316nM | >316nM | 204064 |
| BREAST ADENOCARCINOMA | | | |
| MDA-MB-468 | 78 | 527 | 253 |
| BT-20 | 58 | 207 | 94 |
| MCF-7 | >316nM | >316nM | >316nM |
| COLON ADENOCARCINOMA | | | |
| HT-29 | 7605 | 786 | 669 |
| NORMAL CELL LINES | | | |
| CHO | >316nM | >316nM | >316nM |
| NR-6 | >316nM | >316nM | >316nM |

TABLE 1

```
ATGGCTGCAGCAGTGGTGTCCCATTTTAATGACTGCCCAGATT
CCCACACTCAGTTCTGCTTCCATGGAACATGCAGGTTTTTGGT
GCAGGAGGACAAGCCGGCATGTGTCTGCCATTCTGGGTACGTT
GGTGCGCGCTGTGAGCATGGGACCTCCTGGCTGCTATGGCCGA
AGAGGGCGGCAGCCTGGCCGCGCTGACCGCGCACCAGGCTTGC
CACCTGCCGCTGGAGACTTTCACCCGTCATCGCCAGCCGCGCGG
CTGGGAACAACTGGAGCAGTGCGGCTATCCGGTGCAGCGGCTG
GTCGCCCTCTACCTGGCGGCGCGGCTGTCGTGGAACCAGGTCGA
CCAGGTGATCCGCAACGCCCTGGCCAGCCCCGGCAGCGGCGGC
GACCTGGGCGAAGCGATCCGCGAGCAGCCGGAGCAGGCCCGTC
TGGCCCTGACCCTGGCCGCCGCCGAGAGCGAGCGCTTCGTCCGG
CAGGGCACCGGCAACGACGAGGCCGGCGCGGCCAACGCCGACG
TGGTGAGCCTGACCTGCCCGGTCGCCGCCGGTGAATGCGCGGGC
CCGGCGGACAGCGGCGACGCCCTGCTGGAGCGCAACTATCCCAC
TGGCGCGGAGTTCCTCGGCGACGGCGGCGACGTCAGCTTCAGCA
CCCGCGGCACGCAGAACTGGACGGTGGAGCGGCTGCTCCAGGCG
CACCGCCAACTGGAGGAGCGCGGCTATGTGTTCGTCGGCTACCAC
GGCACCTTCCTCGAAGCGGCGCAAAGCATCGTCTTCGGCGGGGTG
CGCGCGCGCAGCCAGGACCTCGACGCGATCTGGCGCGGTTTCTAT
ATCGCCGGCGATCCGGCGCTGGCCTACGGCTACGCCCAGGACCAG
GAACCCGACGCACGCGGCCGGATCCGCAACGGTGCCCTGCTGCGG
GTCTATGTGCCGCGCTCGAGCCTGCCGGGCTTCTACCGCACCAGCC
TGACCCTGGCCGCGCCGGAGGCGGCGGGCGAGGTCGAACGGCTGA
TCGGCCATCCGCTGCCGCTGCGCCTGGACGCCATCACCGGCCCCGA
GGAGGAAGGCGGGCGCCTGGAGACCATTCTCGGCTGGCCGCTGGCC
GAGCGCACCGTGGTGATTCCCTCGGCGATCCCCACCGACCCGCGCA
ACGTCGGCGGCGACCTCGACCCGTCCAGCATCCCCGACAAGGAACA
GGCGATCAGCGCCCTGCCGGACTACGCCAGCCAGCCCGGCAAACCG
CCGCGCGAGGACCTGAAGTAA
```

TABLE 2

| TGF-alpha-$PE_{40}$ AMINO ACID SEQUENCE | | | | | | | | | | | | | | |
|---|---|---|---|---|---|---|---|---|---|---|---|---|---|---|
| -4 | -3 | -2 | -1 | TGFa[1] | | | 6 | | | | | | | |
| Met | Ala | Ala | Ala | Val | Val | Ser | His | Phe | Asn | Asp | Cys | Pro | Asp | Ser | His | Thr |
| | | | 16 | | | | | | | 26 | | | | |
| Gln | Phe | Cys | Phe | His | Gly | Thr | Cys | Arg | Phe | Leu | Val | Gln | Glu | Asp | Lys |

TABLE 2-continued

TGF-alpha-PE₄₀ AMINO ACID SEQUENCE

|  |  |  |  |  | 36 |  |  |  |  |  |  |  |  | 46 |
|---|---|---|---|---|---|---|---|---|---|---|---|---|---|---|
| Pro | Ala | Cys | Val | Cys | His | Ser | Gly | Tyr | Val | Gly | Ala | Arg | Cys | Glu | His | Ala |

TGFa⁵⁰ PE²⁵²
Asp Leu Leu Ala' Ala Met Ala Glu 'Glu Gly Gly Ser Leu Ala Ala Leu

263
Thr Ala His Gln Ala Cys His Leu Pro Leu Glu Thr Phe Thr Arg His
273

283
Arg Gln Pro Arg Gly Trp Glu Gln Leu Glu Gln Cys Gly Tyr Pro Val 293                                      303
Gln Arg Leu Val Ala Leu Tyr Leu Ala Ala Arg Leu Ser Trp Asn Gln 313                                          323
Val Asp Gln Val Ile Arg Asn Ala Leu Ala Ser Pro Gly Ser Gly Gly

333
Asp Leu Gly Glu Ala Ile Arg Glu Gln Pro Glu Gln Ala Arg Leu Ala 343                                  353
Leu Thr Leu Ala Ala Ala Glu Ser Glu Arg Phe Val Arg Gln Gly Thr

363
Gly Asn Asp Glu Ala Gly Ala Ala Asn Ala Asp Val Val Ser Leu Thr 373                                     383
Cys Pro Val Ala Ala Gly Glu Cys Ala Gly Pro Ala Asp Ser Gly Asp 393                                        403
Ala Leu Leu Glu Arg Asn Tyr Pro Thr Gly Ala Glu Phe Leu Gly Asp

413
Gly Gly Asp Val Ser Phe Ser Thr Arg Gly Thr Gln Asn Trp Thr Val 423                                        433
Glu Arg Leu Leu Gln Ala His Arg Gln Leu Glu Glu Arg Gly Tyr Val

443
Phe Val Gly Tyr His Gly Thr Phe Leu Glu Ala Ala Gln Ser Ile Val Phe 453                              463
Gly Gly Val Arg Ala Arg Ser Gln Asp Leu Asp Ala Ile Trp Arg Gly 473                                   483
Phe Tyr Ile Ala Gly Asp Pro Ala Leu Ala Tyr Gly Tyr Ala Gln Asp

493
Gln Glu Pro Asp Ala Arg Gly Arg Ile Arg Asn Gly Ala Leu Leu Arg

503
Val Tyr Val Pro Arg Ser Ser Leu Pro Gly Phe Tyr Arg Thr Ser Leu
                                                513

523                                     533
Thr Leu Ala Ala Pro Glu Ala Ala Gly Glu Val Glu Arg Leu Ile Gly His

543
Pro Leu Pro Leu Arg Leu Asp Ala Ile Thr Gly Pro Glu Glu Glu Gly 553                                       563
Gly Arg Leu Glu Thr Ile Leu Gly Trp Pro Leu Ala Glu Arg Thr Val

573
Val Ile Pro Ser Ala Ile Pro Thr Asp Pro Arg Asn Val Gly Gly Asp 583                                    593
Leu Asp Pro Ser Ser Ile Pro Asp Lys Glu Gln Ala Ile Ser Ala Leu Pro 603                                       613
Asp Tyr Ala Ser Gln Pro Gly Lys Pro Pro Arg Glu Asp Leu Lys

TABLE 3

TGF-alpha-PE₄₀aB AMINO ACID SEQUENCE

| -4 | -3 | -2 | -1 | 'TGFa¹ |  |  |  |  | 6 |  |  |  |  |  |  |
|---|---|---|---|---|---|---|---|---|---|---|---|---|---|---|---|
| Met | Ala | Ala | Ala | 'Val | Val | Ser | His | Phe | Asn | Asp | Cys | Pro | Asp | Ser | His | Thr |

TABLE 3-continued

TGF-alpha-PE₄₀aB AMINO ACID SEQUENCE

```
              16                                              26
    Gln Phe Cys Phe His Gly Thr Cys Arg Phe Leu Val Gln Glu Asp Lys 36                                      46
    Pro Ala Cys Val Cys His Ser Gly Tyr Val Gly Ala Arg Cys Glu His Ala

TGFa⁵⁰            'PE²⁵²
    Asp Leu Leu Ala' Met Ala Glu 'Glu Gly Gly Ser Leu Ala Ala Leu 264                             274
    Thr Ala His Gln Ala Ala His Leu Pro Leu Glu Thr Phe Thr Arg His

284
    Arg Gln Pro Arg Gly Trp Glu Gln Leu Glu Gln Ala Gly Tyr Pro Val 294                                   304
    Gln Arg Leu Val Ala Leu Tyr Leu Ala Ala Arg Leu Ser Trp Asn Gln

314
    Val Asp Gln Val Ile Arg Asn Ala Leu Ala Ser Pro Gly Ser Gly Gly 324                                       334
    Asp Leu Gly Glu Ala Ile Arg Glu Gln Pro Glu Gln Ala Arg Leu Ala 344                                   354
    Leu Thr Leu Ala Ala Ala Glu Ser Glu Arg Phe Val Arg Gln Gly Thr

364
    Gly Asn Asp Glu Ala Gly Ala Ala Asn Ala Asp Val Val Ser Leu Thr 374                                       384
    Cys Pro Val Ala Ala Gly Glu Cys Ala Gly Pro Ala Asp Ser Gly Asp

394
    Ala Leu Leu Glu Arg Asn Tyr Pro Thr Glu Ala Glu Phe Leu Gly Asp 404                                           414
    Gly Gly Asp Val Ser Phe Ser Thr Arg Gly Thr Gln Asn Trp Thr Val 424                                       434
    Glu Arg Leu Leu Gln Ala His Arg Gln Leu Glu Glu Arg Gly Tyr Val

444
    Phe Val Gly Tyr His Gly Thr Phe Leu Glu Ala Ala Gln Ser Ile Val Phe 454                                   464
    Gly Gly Val Arg Ala Arg Ser Gln Asp Leu Asp Ala Ile Trp Arg Gly 474                                       484
    Phe Tyr Ile Ala Gly Asp Pro Ala Leu Ala Tyr Gly Tyr Ala Gln Asp

494
    Gln Glu Pro Asp Ala Arg Gly Arg Ile Arg Asn Gly Ala Leu Leu Arg 504                                   514
    Val Tyr Val Pro Arg Ser Ser Leu Pro Gly Phe Tyr Arg Thr Ser Leu

524
    Thr Leu Ala Ala Pro Glu Ala Ala Gly Glu Val Glu Arg Leu Ile Gly His 534                                               544
    Pro Leu Pro Leu Arg Leu Asp Ala Ile Thr Gly Pro Glu Glu Glu Gly 554                                   564
    Gly Arg Leu Glu Thr Ile Leu Gly Trp Pro Leu Ala Glu Arg Thr Val

574
    Val Ile Pro Ser Ala Ile Pro Thr Asp Pro Arg Asn Val Gly Gly Asp 584                                       594
    Leu Asp Pro Ser Ser Ile Pro Asp Lys Glu Gln Ala Ile Ser Ala Leu Pro 604                                   614
    Asp Tyr Ala Ser Gln Pro Gly Lys Pro Pro Arg Glu Asp Leu Lys
```

TABLE 4

TGF-alpha-PE₄₀Ab AMINO ACID SEQUENCE

| -4 | -3 | -2 | -1 | TGFa¹ | | | | 6 | | | | | | | |
|---|---|---|---|---|---|---|---|---|---|---|---|---|---|---|---|
| Met | Ala | Ala | Ala | Val | Val | Ser | His | Phe | Asn | Asp | Cys | Pro | Asp | Ser | His | Thr |

| | | 16 | | | | | | | | | 26 | | | |
|---|---|---|---|---|---|---|---|---|---|---|---|---|---|---|
| Gln | Phe | Cys | Phe | His | Gly | Thr | Cys | Arg | Phe | Leu | Val | Gln | Glu | Asp | Lys |

| | | | | 36 | | | | | | | | | | 46 |
|---|---|---|---|---|---|---|---|---|---|---|---|---|---|---|
| Pro | Ala | Cys | Val | Cys | His | Ser | Gly | Tyr | Val | Gly | Ala | Arg | Cys | Glu | His | Ala |

| | TGFa⁵⁰ | | | | | | PE²⁵² | | | | | | |
|---|---|---|---|---|---|---|---|---|---|---|---|---|---|
| Asp | Leu | Leu | Ala | Ala | Met | Ala | Glu | Glu | Gly | Gly | Ser | Leu | Ala | Ala | Leu |

| | | 263 | | | | | | | | 273 | | |
|---|---|---|---|---|---|---|---|---|---|---|---|---|
| Thr | Ala | His | Gln | Ala | Cys | His | Leu | Pro | Leu | Glu | Thr | Phe | Thr | Arg | His |

| | | | | | 283 | | | | | | | |
|---|---|---|---|---|---|---|---|---|---|---|---|---|
| Arg | Gln | Pro | Arg | Gly | Trp | Glu | Gln | Leu | Glu | Gln | Cys | Gly | Tyr | Pro | Val |

| 293 | | | | | | | | | 303 | | | |
|---|---|---|---|---|---|---|---|---|---|---|---|---|
| Gln | Arg | Leu | Val | Ala | Leu | Tyr | Leu | Ala | Ala | Arg | Leu | Ser | Trp | Asn | Gln |

| | | | 313 | | | | | | | | | 323 |
|---|---|---|---|---|---|---|---|---|---|---|---|---|
| Val | Asp | Gln | Val | Ile | Arg | Asn | Ala | Leu | Ala | Ser | Pro | Gly | Ser | Gly | Gly |

| | | | | | 333 | | | | | | | |
|---|---|---|---|---|---|---|---|---|---|---|---|---|
| Asp | Leu | Gly | Glu | Ala | Ile | Arg | Glu | Gln | Pro | Glu | Gln | Ala | Arg | Leu | Ala |

| | | 343 | | | | | | | | 353 | | |
|---|---|---|---|---|---|---|---|---|---|---|---|---|
| Leu | Thr | Leu | Ala | Ala | Ala | Glu | Ser | Glu | Arg | Phe | Val | Arg | Gln | Gly | Thr |

| | | | | 363 | | | | | | | | |
|---|---|---|---|---|---|---|---|---|---|---|---|---|
| Gly | Asn | Asp | Glu | Ala | Gly | Ala | Ala | Asn | Ala | Asp | Val | Val | Ser | Leu | Thr |

| 373 | | | | | | | | | 383 | | | |
|---|---|---|---|---|---|---|---|---|---|---|---|---|
| Ala | Pro | Val | Ala | Ala | Gly | Glu | Ala | Ala | Gly | Pro | Ala | Asp | Ser | Gly | Asp |

| | | | 393 | | | | | | | | | 403 |
|---|---|---|---|---|---|---|---|---|---|---|---|---|
| Ala | Leu | Leu | Glu | Arg | Asn | Tyr | Pro | Thr | Gly | Ala | Glu | Phe | Leu | Gly | Asp |

| | | | | | 413 | | | | | | | |
|---|---|---|---|---|---|---|---|---|---|---|---|---|
| Gly | Gly | Asp | Val | Ser | Phe | Ser | Thr | Arg | Gly | Thr | Gln | Asn | Trp | Thr | Val |

| | | 423 | | | | | | | | 433 | | |
|---|---|---|---|---|---|---|---|---|---|---|---|---|
| Glu | Arg | Leu | Leu | Gln | Ala | His | Arg | Gln | Leu | Glu | Glu | Arg | Gly | Tyr | Val |

| | | | | | 443 | | | | | | | |
|---|---|---|---|---|---|---|---|---|---|---|---|---|
| Phe | Val | Gly | Tyr | His | Gly | Thr | Phe | Leu | Glu | Ala | Ala | Gln | Ser | Ile | Val | Phe |

| 453 | | | | | | | 463 | | | | | |
|---|---|---|---|---|---|---|---|---|---|---|---|---|
| Gly | Gly | Val | Arg | Ala | Arg | Ser | Gln | Asp | Leu | Asp | Ala | Ile | Trp | Arg | Gly |

| | | | 473 | | | | | | | | 483 | |
|---|---|---|---|---|---|---|---|---|---|---|---|---|
| Phe | Tyr | Ile | Ala | Gly | Asp | Pro | Ala | Leu | Ala | Tyr | Gly | Tyr | Ala | Gln | Asp |

| | | | | | 493 | | | | | | | |
|---|---|---|---|---|---|---|---|---|---|---|---|---|
| Gln | Glu | Pro | Asp | Ala | Arg | Gly | Arg | Ile | Arg | Asn | Gly | Ala | Leu | Leu | Arg |

| | 503 | | | | | | | | 513 | | | |
|---|---|---|---|---|---|---|---|---|---|---|---|---|
| Val | Tyr | Val | Pro | Arg | Ser | Ser | Leu | Pro | Gly | Phe | Tyr | Arg | Thr | Ser | Leu |

| | | | | 523 | | | | | | | | 533 |
|---|---|---|---|---|---|---|---|---|---|---|---|---|
| Thr | Leu | Ala | Ala | Pro | Glu | Ala | Ala | Gly | Glu | Val | Glu | Arg | Leu | Ile | Gly | His |

| | | | | | | | 543 | | | | | |
|---|---|---|---|---|---|---|---|---|---|---|---|---|
| Pro | Leu | Pro | Leu | Arg | Leu | Asp | Ala | Ile | Thr | Gly | Pro | Glu | Glu | Glu | Gly |

| | 553 | | | | | | | | | 563 | | |
|---|---|---|---|---|---|---|---|---|---|---|---|---|
| Gly | Arg | Leu | Glu | Thr | Ile | Leu | Gly | Trp | Pro | Leu | Ala | Glu | Arg | Thr | Val |

| | | | | | 573 | | | | | | | |
|---|---|---|---|---|---|---|---|---|---|---|---|---|
| Val | Ile | Pro | Ser | Ala | Ile | Pro | Thr | Asp | Pro | Arg | Asn | Val | Gly | Gly | Asp |

| 583 | | | | | | | | | 593 | | | |
|---|---|---|---|---|---|---|---|---|---|---|---|---|
| Leu | Asp | Pro | Ser | Ser | Ile | Pro | Asp | Lys | Glu | Gln | Ala | Ile | Ser | Ala | Leu | Pro |

| | | | 603 | | | | | | | | 613 | |
|---|---|---|---|---|---|---|---|---|---|---|---|---|
| Asp | Tyr | Ala | Ser | Gln | Pro | Gly | Lys | Pro | Pro | Arg | Glu | Asp | Leu | Lys |

TABLE 5

TGF-alpha-PE$_{40}$ab AMINO ACID SEQUENCE

| -4 | -3 | -2 | -1 | TGFa$^1$ | | | | | 6 | | | | | |
|---|---|---|---|---|---|---|---|---|---|---|---|---|---|---|
| Met | Ala | Ala | Ala | Val | Val | Ser | His | Phe | Asn | Asp | Cys | Pro | Asp | Ser | His | Thr |

| | | 16 | | | | | | | | 26 | | | |
|---|---|---|---|---|---|---|---|---|---|---|---|---|---|
| Gln | Phe | Cys | Phe | His | Gly | Thr | Cys | Arg | Phe | Leu | Val | Gln | Glu | Asp | Lys |

| | | | | 36 | | | | | | | | | 46 |
|---|---|---|---|---|---|---|---|---|---|---|---|---|---|
| Pro | Ala | Cys | Val | Cys | His | Ser | Gly | Tyr | Val | Gly | Ala | Arg | Cys | Glu | His | Ala |

| | | TGFa$^{50}$ | | | | PE$^{252}$ | | | | | | | |
|---|---|---|---|---|---|---|---|---|---|---|---|---|---|
| Asp | Leu | Leu | Ala' | Met | Ala | Glu | 'Glu | Gly | Gly | Ser | Leu | Ala | Ala | Leu |

| | | | 264 | | | | | | | | 274 | | |
|---|---|---|---|---|---|---|---|---|---|---|---|---|---|
| Thr | Ala | His | Gln | Ala | Ala | His | Leu | Pro | Leu | Glu | Thr | Phe | Thr | Arg | His |

| | | | | | | | 284 | | | | | | |
|---|---|---|---|---|---|---|---|---|---|---|---|---|---|
| Arg | Gln | Pro | Arg | Gly | Trp | Glu | Gln | Leu | Glu | Gln | Ala | Gly | Tyr | Pro | Val |

| | 294 | | | | | | | | | 304 | | | |
|---|---|---|---|---|---|---|---|---|---|---|---|---|---|
| Gln | Arg | Leu | Val | Ala | Leu | Tyr | Leu | Ala | Ala | Arg | Leu | Ser | Trp | Asn | Gln |

| | | | | 314 | | | | | | | | | |
|---|---|---|---|---|---|---|---|---|---|---|---|---|---|
| Val | Asp | Gln | Val | Ile | Arg | Asn | Ala | Leu | Ala | Ser | Pro | Gly | Ser | Gly | Gly |

| 324 | | | | | | | | | 334 | | | | |
|---|---|---|---|---|---|---|---|---|---|---|---|---|---|
| Asp | Leu | Gly | Glu | Ala | Ile | Arg | Glu | Gln | Pro | Glu | Gln | Ala | Arg | Leu | Ala |

| | | | 344 | | | | | | | | | 354 | |
|---|---|---|---|---|---|---|---|---|---|---|---|---|---|
| Leu | Thr | Leu | Ala | Ala | Ala | Glu | Ser | Glu | Arg | Phe | Val | Arg | Gln | Gly | Thr |

| | | | | | | 364 | | | | | | | |
|---|---|---|---|---|---|---|---|---|---|---|---|---|---|
| Gly | Asn | Asp | Glu | Ala | Gly | Ala | Ala | Asn | Ala | Asp | Val | Val | Thr | Leu | Thr |

| | 374 | | | | | | | | | 384 | | | |
|---|---|---|---|---|---|---|---|---|---|---|---|---|---|
| Ala | Pro | Val | Ala | Ala | Gly | Glu | Ala | Ala | Gly | Pro | Ala | Asp | Ser | Gly | Asp |

| | | | | 394 | | | | | | | | | |
|---|---|---|---|---|---|---|---|---|---|---|---|---|---|
| Ala | Leu | Leu | Glu | Arg | Asn | Tyr | Pro | Thr | Gly | Ala | Glu | Phe | Leu | Gly | Asp |

| 404 | | | | | | | | | 414 | | | | |
|---|---|---|---|---|---|---|---|---|---|---|---|---|---|
| Gly | Gly | Asp | Val | Ser | Phe | Ser | Thr | Arg | Gly | Thr | Gln | Asn | Trp | Thr | Val |

| | | | 424 | | | | | | | | 434 | | |
|---|---|---|---|---|---|---|---|---|---|---|---|---|---|
| Glu | Arg | Leu | Leu | Gln | Ala | His | Arg | Gln | Leu | Glu | Glu | Arg | Gly | Tyr | Val |

| | | | | | | 444 | | | | | | | |
|---|---|---|---|---|---|---|---|---|---|---|---|---|---|
| Phe | Val | Gly | Tyr | His | Gly | Thr | Phe | Leu | Glu | Ala | Ala | Gln | Ser | Ile | Val | Phe |

| | 454 | | | | | | | | | 464 | | | |
|---|---|---|---|---|---|---|---|---|---|---|---|---|---|
| Gly | Gly | Val | Arg | Ala | Arg | Ser | Gln | Asp | Leu | Asp | Ala | Ile | Trp | Arg | Gly |

| | | | | 474 | | | | | | | | | 484 |
|---|---|---|---|---|---|---|---|---|---|---|---|---|---|
| Phe | Tyr | Ile | Ala | Gly | Asp | Pro | Ala | Leu | Ala | Tyr | Gly | Tyr | Ala | Gln | Asp |

| | | | | | | | 494 | | | | | | |
|---|---|---|---|---|---|---|---|---|---|---|---|---|---|
| Gln | Glu | Pro | Asp | Ala | Arg | Gly | Arg | Ile | Arg | Asn | Gly | Ala | Leu | Leu | Arg |

| | | 504 | | | | | | | | | 514 | | |
|---|---|---|---|---|---|---|---|---|---|---|---|---|---|
| Val | Tyr | Val | Pro | Arg | Ser | Ser | Leu | Pro | Gly | Phe | Tyr | Arg | Thr | Ser | Leu |

| | | | | 524 | | | | | | | | | |
|---|---|---|---|---|---|---|---|---|---|---|---|---|---|
| Thr | Leu | Ala | Ala | Pro | Glu | Ala | Ala | Gly | Glu | Val | Glu | Arg | Leu | Ile | Gly | His |

| 534 | | | | | | | | | 544 | | | | |
|---|---|---|---|---|---|---|---|---|---|---|---|---|---|
| Pro | Leu | Pro | Leu | Arg | Leu | Asp | Ala | Ile | Thr | Gly | Pro | Glu | Glu | Glu | Gly |

| | | | 554 | | | | | | | | 564 | | |
|---|---|---|---|---|---|---|---|---|---|---|---|---|---|
| Gly | Arg | Leu | Glu | Thr | Ile | Glu | Gly | Trp | Pro | Leu | Ala | Glu | Arg | Thr | Val |

| | | | | | | 574 | | | | | | | |
|---|---|---|---|---|---|---|---|---|---|---|---|---|---|
| Val | Ile | Pro | Ser | Ala | Ile | Pro | Thr | Asp | Pro | Arg | Asn | Val | Gly | Gly | Asp |

| | 584 | | | | | | | | | 594 | | | |
|---|---|---|---|---|---|---|---|---|---|---|---|---|---|
| Leu | Asp | Pro | Ser | Ser | Ile | Pro | Asp | Lys | Glu | Gln | Ala | Ile | Ser | Ala | Leu | Pro |

| | | | | 604 | | | | | | | | | 614 |
|---|---|---|---|---|---|---|---|---|---|---|---|---|---|
| Asp | Tyr | Ala | Ser | Gln | Pro | Gly | Lys | Pro | Pro | Arg | Glu | Asp | Leu | Lys |

What is claimed is:

1. A method of treating bladder cancer comprising administering to a patient having bladder cancer a therapeutically effective amount of a hybrid protein selected from the group consisting of TGF-alpha-$PE_{40}$Ab, TGF-alpha-$PE_{40}$aB and TGF-alpha-$PE_{40}$ab, wherein "a" and "b" represent substitution of the cysteine residues at the A and B locus, respectively, with alanine or glycine residues.

2. A method according to claim 1 wherein the hybrid protein is in the form of a solution or suspension in a physiologically acceptable liquid.

3. A method according to claim 2 wherein the liquid comprises sterile water, water for injection, saline or buffered saline.

4. A method according to claim 3 wherein the liquid comprises buffered saline and additionally comprises a carrier protein.

5. A method according to claim 4 wherein the liquid is phosphate buffered saline and the carrier protein is human serum albumin.

6. A method according to claim 5 wherein the phosphate buffered saline contains from about 0.1 mg to about 10 mg of hybrid protein per 60 ml.

7. A method according to claim 5 wherein the phosphate buffered saline contains from about 0.5 mg to about 5 mg of the hybrid protein per 60 ml.

8. A method according to claim 5 wherein the phosphate buffered saline contains from about 2 mg to about 4 mg of the hybrid protein per 60 ml.

9. A method according to claim 2 wherein the physiologically acceptable liquid contains from about 0.1 mg to about 10 mg of the hybrid protein per 60 ml.

10. A method according to claim 2 wherein the physiologically acceptable liquid contains from about 0.5 mg to about 5 mg of the hybrid protein per 60 ml.

11. A method according to claim 2 wherein the physiologically acceptable liquid contains from about 2 mg to about 4 mg of the hybrid protein per 60 ml.

12. A method according to claim 2 wherein the administering is continued for a period of from about 30 minutes to about 4 hours.

13. A method according to claim 2 wherein the administering takes place at physiological temperature.

14. The method according to claim 1 wherein the hybrid protein is prepared by a urea-free process that comprises the purification step of precipitating the crude hybrid protein from a solution with ammonium sulfate.

15. A urea-free process for the preparation of a TGF-alpha-$PE_{40}$ hybrid protein comprising the steps of harvesting a sufficient quantity of cells expressing a hybrid protein selected from the group consisting of TGF-alpha-$PE_{40}$Ab, TGF-alpha-$PE_{40}$aB and TGF-alpha-$PE_{40}$ab wherein "a" and "b" represent substitution of the cysteine residues at the A and B locus, respectively, with alanine or glycine residues;
   precipitating the expressed hybrid protein with ammonium sulfate;
   solublizing the precipitated protein; and
   purifying the soluble protein by affinity chromatography using a metal chelating chromatography column.

16. A hybrid protein prepared by the process of claim 15.

17. The hybrid protein of claim 16, wherein said hybrid protein is either TGF-alpha-$PE_{40}$ab or TGF-alpha-$PE_{40}$aB.

18. The method of claim 15 wherein the expressed hybrid protein is TGF-alpha-$PE_{40}$aB.

19. The method of claim 15 wherein the expressed hybrid protein is TGF-alpha-$PE_{40}$ab.

20. The method of claim 15 wherein the expressed hybrid protein is TGF-alpha-$PE_{40}$Ab.

* * * * *